United States Patent [19]

Barnhart et al.

[11] Patent Number: 5,762,952
[45] Date of Patent: Jun. 9, 1998

[54] TRANSDERMAL DELIVERY OF ACTIVE DRUGS

[75] Inventors: Scott D. Barnhart, York; Elio P. Mariani, Lancaster, both of Pa.

[73] Assignee: Hercon Laboratories Corporation, New York, N.Y.

[21] Appl. No.: 52,768

[22] Filed: Apr. 27, 1993

[51] Int. Cl.$^6$ .................................................. A61F 13/02
[52] U.S. Cl. ........................................ 424/448; 424/449
[58] Field of Search .................................. 424/448, 449

[56] References Cited

U.S. PATENT DOCUMENTS

| | | | |
|---|---|---|---|
| 3,797,494 | 3/1974 | Zaffaroni | 128/268 |
| 3,921,636 | 11/1975 | Zaffaroni | 128/260 |
| 4,409,206 | 10/1983 | Stricker et al. | 424/81 |
| 4,421,737 | 12/1983 | Ito et al. | 424/28 |
| 4,482,534 | 11/1984 | Blank | 424/28 |
| 4,505,891 | 3/1985 | Ito | 424/28 |
| 4,608,249 | 8/1986 | Otsuka et al. | 424/28 |
| 4,615,699 | 10/1986 | Gale et al. | 604/897 |
| 4,675,009 | 6/1987 | Hymes et al. | 604/304 |
| 4,696,821 | 9/1987 | Belsole | 424/448 |
| 4,746,515 | 5/1988 | Cheng et al. | 424/449 |
| 4,751,087 | 6/1988 | Wick | 424/449 |
| 4,758,434 | 7/1988 | Kydonieus et al. | 424/449 |
| 4,814,168 | 3/1989 | Sablotsky et al. | 424/78 |
| 4,863,738 | 9/1989 | Taskovich | 424/449 |
| 4,889,721 | 12/1989 | Ueda et al. | 424/448 |
| 4,908,213 | 3/1990 | Govil et al. | 424/447 |
| 4,911,916 | 3/1990 | Cleary | 424/449 |
| 4,915,102 | 4/1990 | Kwiatek et al. | 128/156 |
| 4,943,435 | 7/1990 | Baker et al. | 424/448 |
| 4,946,853 | 8/1990 | Bannon et al. | 514/343 |
| 4,994,267 | 2/1991 | Sablotsky | 424/78 |
| 5,028,435 | 7/1991 | Katz et al. | 424/484 |
| 5,122,383 | 6/1992 | Heiber | 424/449 |
| 5,133,821 | 7/1992 | Jensen | 156/245 |
| 5,133,970 | 7/1992 | Petereit et al. | 424/443 |
| 5,145,682 | 9/1992 | Chien et al. | 424/448 |
| 5,154,929 | 10/1992 | Shibata et al. | 424/448 |
| 5,200,190 | 4/1993 | Azuma et al. | 424/443 |
| 5,202,125 | 4/1993 | Ebert | 424/449 |
| 5,204,109 | 4/1993 | Akemi et al. | 424/443 |
| 5,240,711 | 8/1993 | Hille et al. | 424/448 |
| 5,242,951 | 9/1993 | Akemi et al. | 514/772.5 |
| 5,298,258 | 3/1994 | Akemi et al. | 424/484 |
| 5,554,381 | 9/1996 | Roos et al. | 424/449 |
| 5,560,922 | 10/1996 | Chien et al. | 424/448 |

FOREIGN PATENT DOCUMENTS

| | | |
|---|---|---|
| 930668 | 7/1973 | Canada. |
| 1136045 | 11/1983 | Canada. |
| 2006398 | 6/1990 | Canada. |
| 2027053 | 4/1991 | Canada. |
| A2-0237263 | 9/1987 | European Pat. Off.. |
| 0421454 | 4/1991 | European Pat. Off.. |
| 0430019 | 6/1991 | European Pat. Off.. |
| 0435199 | 7/1991 | European Pat. Off.. |
| 0435200 | 7/1991 | European Pat. Off.. |
| 0436203 | 7/1991 | European Pat. Off.. |
| A3-0455458 | 12/1991 | European Pat. Off.. |
| 0518113 | 12/1992 | European Pat. Off.. |
| 3843238 | 2/1990 | Germany. |
| 57-7409 | 1/1982 | Japan ............. A61K 9/70 |
| 57-7413 | 1/1982 | Japan ............. A61K 9/70 |
| 57-7414 | 1/1982 | Japan ............. A61K 9/70 |
| 58-46959 | 3/1983 | Japan ............. A61L 15/06 |
| 8600814 | 2/1986 | WIPO. |
| 9205811 | 4/1992 | WIPO. |

OTHER PUBLICATIONS

Database WPI, Week 8251, Derwent Publications Ltd., London, GB, AN 82–10519j for JP-A-57-185223 (Nov. 15, 1982).

*Primary Examiner*—D. Gabrielle Phelan
*Attorney, Agent, or Firm*—Sughrue, Mion, Zinn, Macpeak & Seas, PLLC

[57] ABSTRACT

A transdermal delivery system is described, including a backing layer having coated thereon an active drug-containing adhesive layer which includes (a) an acrylic-based adhesive which is self-crosslinking at a temperature of from about 20° C. to about 65° C. and (b) an active drug. A method for manufacturing a transdermal delivery system is also described, including (A) mixing an active drug with an acrylic-based adhesive solution which is self-crosslinking at a temperature of from about 20° C. to about 65° C. to form an active drug-adhesive mixture, (B) forming a coating of the active drug-adhesive mixture on a backing layer, and (C) drying the coating to form an active drug-containing adhesive layer. Examples of the active drug include nitroglycerin and estradiol.

33 Claims, No Drawings

TRANSDERMAL DELIVERY OF ACTIVE DRUGS

FIELD OF THE INVENTION

This invention relates to articles of manufacture for the delivery of an active drug transdermally and to a method for the manufacture thereof. In particular, this invention relates to a system useful for the efficacious delivery of an active drug, such as nitroglycerin or estradiol, transdermally and to a method for the manufacture thereof.

BACKGROUND OF THE INVENTION

Numerous patents have issued for the delivery of active drugs, such as the delivery of nitroglycerin to the skin in the treatment of angina pectoris and/or the treatment of congestive heart failure.

Some formulations require complex reservoirs, such as encapsulated or walled containers having interior drug-containing chambers (e.g., microcapsules) and/or multiple layers, as described by Zaffaroni in Canadian Patent 930668.

Other transdermal systems require a drug-loaded matrix, as disclosed by Zaffaroni in U.S. Pat. No. 3,921,636 and by Kydonieus et al in U.S. Pat. No. 4,758,434 describing prior Hercon technology. The prior Hercon technology is directed to a PVC plastisol, and both the Zaffaroni and Kydonieus patents utilize a drug loaded polymeric matrix which acts as the reservoir. Thus, neither transdermal system adheres to the skin by itself, but rather requires the assistance of a pressure-sensitive adhesive, located around the periphery of the reservoir or as a separate layer covering the face of the reservoir, for attachment to the patient.

Transdermal devices having nitroglycerin intimately dispersed or solubilized within an adhesive polymer or copolymer are described by Ito et al in U.S. Pat. No. 4,421,737, by Ito in U.S. Pat. No. 4,505,891, by Wick in U.S. Pat. No. 4,751,087, by Stricker et al in U.S. Pat. No. 4,409,206, and by Sablotsky in PCT Application WO86/00314. The nitroglycerin-containing adhesive is subsequently coated onto an impervious backing sheet.

Ito et al (U.S. Pat. No. 4,421,737) describes a pressure-sensitive medicinal adhesive tape or sheet containing nitroglycerin in which a tackified rubber-based adhesive is coated onto a backing. Softeners for rubber-based adhesives (e.g., mineral oil, long chain fatty acid esters, lanolin derivatives, and hydrogenated fats and oils) and nitroglycerin must be added in a separate coating step. This separate step requires that the coatings come into intimate contact while aging the material at an elevated temperature, thus allowing for the nitroglycerin and softeners to be transferred together to the rubber-based adhesive through diffusion. The manufacture of such an article would be highly labor intensive and may tend to vary from lot to lot. Additionally, Ito et al discloses the use of antioxidants in the rubber-based formulation. It is well documented in the literature as to the high incidence of human allergic responses to rubber-based adhesives and particularly to the additives (i.e., antioxidants and tackifiers) which are routinely used to formulate this class of adhesives. Also, Ito et al discloses that only 1–10 weight percent of nitroglycerin is incorporated with respect to the total dry adhesive weight.

Ito (U.S. Pat. No. 4,505,891) describes a pressure-sensitive medicinal adhesive tape or sheet containing nitroglycerin, in which nitroglycerin is incorporated into a copolymer of dodecyl methacrylate and a functional monomer in an amount to yield a content of 1–20 mg, preferably 5–15 mg, per 100 $cm^2$. Such copolymers are the basis for acrylic pressure-sensitive adhesive technology. However, assuming that the greatest nitroglycerin loading disclosed in Ito is used (20 mg/100 $cm^2$), the size of the nitroglycerin system needed to produce a therapeutically effective dose would be extremely large. A transdermal system of this size would also be very uncomfortable to wear.

Other nitroglycerin transdermal formulations employ skin penetration enhancers, such as long chain fatty acid esters (e.g., isopropyl myristate and ethyl oleate) and fatty acid monoglycerides (e.g., glycerol monostearate) as described by Wick in U.S. Pat. No. 4,751,087. The penetration enhancers are needed when the nitroglycerin flux from the delivery system is not high enough by itself to provide a sufficiently high rate of diffusion of nitroglycerin into the skin. However, a certain percentage of the population will show signs of contact dermatitis to any chemical, so if any components can be eliminated from a formulation, the probability of an allergic response is reduced.

The Wick patent discloses an adhesive-coated sheet material comprising a flexible backing and a pressure-sensitive adhesive coating comprising a homogeneous mixture of an acrylic polymer and nitroglycerin in an amount by weight of about 25–45 weight percent of the total weight of the adhesive coating. To assist in the delivery of the nitroglycerin, Wick discloses that the adhesive-coated sheet material can comprise a homogeneous mixture of an acrylic polymer and a skin penetration enhancing combination comprising ethyl oleate and glycerol monolaurate.

Stricker et al in U.S. Pat. No. 4,409,206 formulated a number of different pharmaceutically active compounds, including nitroglycerin, into an adhesive material such as an acrylic polymer. However, there is no disclosure with respect to how to incorporate large percentages of a polymer-solubilizing agent such as nitroglycerin without a deleterious reduction of the adhesive properties of the polymer.

Sablotsky in PCT Application WO 86/00814 approaches the problem of incorporating large percentages of nitroglycerin into adhesive polymers by using a thermally activated catalyst to crosslink the acrylic adhesive. However, there is evidence that nitroglycerin is volatized at elevated temperatures, as seen by the increase in vapor pressure with increasing temperature, and thermally activated catalysts require sufficient heat to overcome the energy barrier of catalyzing the cross-linking reaction. This heat, in the form of elevated temperatures, results in a loss of nitroglycerin during processing due to volatilization. This causes the nitroglycerin content to vary in the finished product, due to the lack of control over evaporation of the nitroglycerin. The method for making the Sablotsky system also can be very hazardous. It is noted that Sablotsky specifically requires one practicing the invention to add the crosslinking agent after the adhesive acrylate polymer and the pharmaceutically active drug are mixed thoroughly, so the nitroglycerin will be present when the temperature is raised.

SUMMARY OF THE INVENTION

In view of the above problems in the art, one object of the present invention is to provide a transdermal delivery system in which an active drug, such as nitroglycerin or estradiol, is contained directly in the adhesive in the system.

A second object of the present invention is to provide a transdermal delivery system which does not cause a high incidence of human allergic responses such as contact dermatitis.

A third object of the present invention is to provide a transdermal delivery system in which the adhesive contains a sufficiently large amount of an active drug, so the size of the system needed to produce a therapeutically effective dose is small enough to be comfortable to wear.

A fourth object of the present invention is to provide a transdermal delivery system in which a large amount of an active drug or inactive excipient is incorporated into the adhesive polymer without a deleterious reduction of the adhesive properties of the polymer.

A fifth object of the present invention is to provide a method of manufacturing a transdermal delivery system which enables the production of a system containing a large amount of an active drug or inactive excipient.

A sixth object of the present invention is to provide a method of manufacturing a transdermal delivery system which is not highly labor intensive.

A seventh object of the present invention is to provide a method of manufacturing a transdermal delivery system which avoids variations in the active drug content in the finished product.

An eighth object of the present invention is to provide a method of manufacturing a transdermal delivery system which is relatively safe to practice.

The above and other objects of the present invention are attained by a transdermal delivery system comprising a backing layer having coated thereon an active drug-containing adhesive layer comprising (a) an acrylic-based adhesive which is self-crosslinking at a temperature of from about 20° C. to about 65° C., and (b) an active drug, and by a method of manufacturing an active drug transdermal delivery system, wherein the method comprises (A) mixing an active drug with an acrylic-based adhesive solution which is self-crosslinking at a temperature of from about 20° C. to about 650° C. to form an active drug-adhesive mixture;

(B) forming a coating of the active drug-adhesive mixture on a backing layer; and (C) drying the coating to form an active drug-containing adhesive layer.

DETAILED DESCRIPTION OF THE INVENTION

The present invention is directed to an article of manufacture which is useful for the efficacious delivery of an active drug transdermally and to a method for the manufacture thereof.

The components of the transdermal delivery system are described in detail below.

A key component of the transdermal delivery system is the acrylic-based adhesive which is self-crosslinking at room temperature (about 20° C. to about 30° C.) or at a temperature which is elevated slightly above room temperature (about 30° C. to about 65° C.). The present inventors discovered that by employing an acrylic-based adhesive which is self-crosslinking at a temperature of from about 20° C. to about 65° C. (hereinafter referred to as a self-crosslinking adhesive), the problems associated with acrylic adhesives in which a thermally-activated catalyst is used for crosslinking (e.g., loss of nitroglycerin during processing due to volatilization, causing the nitroglycerin content to vary in the finished product and leading to a very hazardous situation) can be avoided, while permitting a large amount of the active drug to be incorporated into the adhesive.

The self-crosslinking adhesive used in the present invention is a pressure sensitive adhesive suitable for medical applications. The adhesive serves to hold the transdermal delivery system in contact with the skin, so that the active drug can diffuse from the transdermal delivery system into the skin. Also, the adhesive acts as a reservoir for the active drug.

Self-crosslinking adhesives (i.e., adhesives which are curable at room temperature or at slightly elevated temperatures) and their use in pressure sensitive adhesive articles are described in detail in U.S. Pat. Nos. 3,886,126 and 3,900,610, which are incorporated herein by reference. One can also refer to U.S. Pat. No. 3,532,708, British Patent 1,448,937, and Canadian Patent 1,126,893 for descriptions of self-crosslinking adhesives.

High molecular weight synthetic polymers, such as esters of acrylic acid, can undergo crosslinking with any group offering an available active hydrogen, such as amido, amino, carboxyl, hydroxyl and thio groups. Hydroxy crosslinking can take place between one functionalized polymer and another functionalized polymer through any combination of the active hydrogens of the respective polymer's functional groups. These reactions yield resins and coatings with improved hardness and solvent resistance, and may allow for the incorporation of a high-boiling solvent, such as a plasticizer, a permeation enhancer or drug substance, without dissolution or degradation of the polymer itself. The extent of the crosslinking is governed in part by steric considerations regarding the availability of active functional groups on the polymer chain and by the energy barriers required to initiate the crosslinking reaction. Metal catalysts resistant to hydrolysis can be mixed with crosslinkable materials at room temperature without premature crosslinking, provided a material such as isopropanol is present in excess to maintain the chemical structure of the catalyst during the equilibrium reaction that occurs over time. The reaction can be forced to completion by driving off the lower boiling by-product. If the metal catalyst is present in molar quantities sufficiently below its saturation point, the catalyst would be completely contained within the dried polymer as a result of the crosslinking and there would be no migration of excess catalyst out of the dried polymer. Physical testing such as peel adhesion and plasticity demonstrates property differences as crosslinker levels vary.

Adhesives suitable for the present invention can have esters of $C_4$–$C_{10}$ alkyl alcohols as their main component. However, the amount of these esters can be substantially less than 80% by weight. For instance, the adhesives can contain less than 70% by weight of the esters of $C_4$–$C_{10}$ alkyl alcohols.

Suitable self-crosslinking acrylic-based adhesives which are commercially available include Gelva® Multipolymer Resin Solutions (GMS) 1753, 2257, and 2465, manufactured by the Monsanto Company, St. Louis, Mo., and Aroset 1910-TH-52, Aroset 1930-TH-48, and Aroset-1880-Z-46, manufactured by Ashland Chemical Co., Columbus, Ohio. For example, GMS 2465 is a self-curable adhesive which develops full properties upon evaporation of the solvent phase and exhibits good adhesion to a variety of substrates, including plastic substrates such as polyvinyl chloride and polyester. In particular, this high performance, self-crosslinking acrylic polymer is supplied at 44% solids in a mixture of ethyl acetate and isopropanol and has a Brookfield LVF viscosity of 3000–6000 cps at 25° C., appropriate for knife or roll coating.

An important advantage resulting from the use of a self-crossliniking acrylic-based adhesive is the ability to incorporate either a large amount of the active drug or a large amount of an inactive solubilizing agent into the adhesive. For instance, a large amount of nitroglycerin can be incorporated into the adhesive. In fact, the amount of nitroglycerin which can be present in the nitroglycerin transdermal delivery system of the present invention is significantly higher than the maximum amount of nitroglycerin presently incorporated in nitroglycerin transdermal delivery systems known in the art. For example, nitroglycerin can be present in the invention nitroglycerin transdermal delivery system in an amount of at least 50% by weight, based on the total dry weight of the adhesive layer. Indeed, nitroglycerin can be present in the invention nitroglycerin transdermal delivery system in an amount of at least 55% by weight, at least 60% by weight, or at least 65% by weight, based on the total dry weight of the adhesive layer. The upper limit to be used is dependent on safety and handling considerations because of the nature of nitroglycerin in regard to shock hazards.

A preferred nitroglycerin content ranges from 50–65% by weight, more preferably from 55–65% by weight, based on the total dry weight of the adhesive layer. Of course, smaller amounts of nitroglycerin can also be employed in the present invention, such as at least 20% by weight. The minimum concentration of nitroglycerin can be reduced to levels less than 20% by weight, but the issue of therapeutic availability arises. If a transdermal delivery system has a low nitroglycerin content, the ultimate size of the system may be impractical for the consumer to use, since nitroglycerin content is related to concentration per surface area.

The present invention is also very useful for the transdermal delivery of estradiol. An advantage resulting from the use of the self-crosslinking adhesive of the present invention is that a skin permeation enhancer employed in the system with the estradiol can be present in a large amount. In fact, the amount of permeation enhancer which can be present in the estradiol transdermal delivery system of the present invention is significantly higher than the maximum amount of permeation enhancers presently incorporated in monolithic transdermal delivery systems known in the art. For example, permeation enhancers can be present in the invention estradiol transdermal delivery system in an amount of up to 60% by weight, based on the total dry weight of the adhesive layer. Indeed, permeation enhancers can be present in the invention estradiol transdermal delivery system in a general range of from 2 to 60%. A preferred range is from 5 to 50%, and a more preferred range is from 25 to 45%, based on the total dry weight of the adhesive layer. The upper limit to be used is dependent on saturation solubilities of the respective permeation enhancer in the self-crosslinking adhesive polymer, resulting in phase separation.

Estradiol can be present in the transdermal delivery system of the present invention in an amount of at least 0.1% by weight, preferably at least 1.0% by weight, more preferably at least 2.5% by weight, based on the total dry weight of the adhesive layer. A preferred estradiol content ranges from 0.1 to 4.5% by weight, more preferably from 1.0 to 4.0% by weight, based on the total dry weight of the adhesive layer.

Other active drugs which can be used in other transdermal delivery systems can also be used in the present invention. For example, nicotine is a suitable active drug for use in the present invention. Also, suitable active drugs include fentanyl, clonidine, isosorbide dinitrate, indomethacin, guanfacine, and prostaglandins. Other suitable active drugs include reproductive-related steroids such as progestin. Still other suitable active drugs include benzodiazepines, such as alprazolam. The active drug can be present in an amount of at least 0.01% by weight, preferably at least 0.5% by weight, more preferably at least 1.0% by weight, based on the total dry weight of the adhesive layer. A preferred active drug content ranges from 0.01 to 65% by weight, more preferably from 0.5 to 50% by weight, based on the total dry weight of the adhesive layer.

The active drug-adhesive mixture is coated on a backing layer. Backing layers well known in the art can be used in the present invention. The backing layer can be a flexible substrate which provides a barrier to the active drug migration away from the intended direction of drug delivery, and any well-known backing layer which satisfies this purpose can be used in the present invention. For example, a polyester film can be used as the backing layer.

The transdermal delivery system can include an impervious release liner, which serves to protect the active drug-containing adhesive layer prior to application. Any well-known release liner which satisfies this purpose can be used in the present invention. For example, a polyester film which has been coated with silicone on one or both sides can be used as the release liner. The release liner should desirably not absorb significant amounts of the active drug.

Other components which can be present in this invention include skin permeation enhancers such as alkyl methyl sulfoxides, saturated fatty acid alkyl esters, unsaturated fatty acid alkyl esters, cyclic saturated ketones, and $C_1$ to $C_{14}$ aliphatic linear and branched chain alcohols. Some of these enhancers may include isopropyl palmitate, isopropyl myristate, propyl oleate, decylmethyl sulfoxide, propylene glycol, hexylene glycol, oleic acid, and myristyl alcohol.

It should be noted that various components which are often required in other transdermal delivery systems (e.g., permeation enhancers) are not needed for embodiments of the present invention such as the nitroglycerin system, due to the superior properties of the present invention (e.g., a high nitroglycerin flux from the delivery system). Thus, problems in the art (e.g., an allergic response and/or skin irritation due to permeation enhancers) can be avoided by the present invention.

One embodiment of the present invention contains the active drug incorporated into a self-crosslinking acrylic multipolymer adhesive coated onto a flexible barrier film and protected by an impervious release liner. A preferred embodiment of this invention is directed to an article having a flexible substrate providing a barrier to nitroglycerin migration away from the intended direction of drug delivery, an acrylic multipolymer adhesive provided on the substrate containing a catalyst for crosslinking the adhesive at room temperature, 50–65% w/w nitroglycerin incorporated into the adhesive solids, and a protective impervious release liner which does not absorb significant amounts of nitroglycerin while allowing for complete removal from the transdermal drug delivery system with no residue.

The present invention is used to administer an active drug to a patient. The active drug is administered by applying the transdermal delivery system of the present invention to the patient's skin, where the adhesive layer of the system affixes the system to the skin. The active drug diffuses from the adhesive layer into the skin. With the transdermal delivery system of the present invention, it is possible to obtain a high in vitro transdermal flux. For instance, with respect to the delivery of nitroglycerin, it is possible to obtain an in vitro transdermal flux ranging from, for example, 30 $\mu g/cm^2/hr$ to 70 $\mu g/cm^2/hr$, without the use of a skin permeation enhancer. Additionally, with respect to the delivery of estradiol, it is possible to obtain an in vitro transdermal flux ranging from, for example, 0.02 µg/cm²/hr to 0.90 µg/cm²/hr, with the aid of a permeation enhancer without compromising the adhesive properties of the present invention.

The method for manufacturing the transdermal delivery system of the present invention includes the steps of mixing the active drug(s) with a self-crosslinking acrylic-based adhesive solution to form an active drug-adhesive mixture, forming a coating of the active drug-adhesive mixture on a backing layer, and drying the coating to form an active drug-containing adhesive layer.

With respect to the nitroglycerin embodiment in particular, the present inventors discovered that by using a self-crosslinking acrylic-based adhesive solution and mixing the nitroglycerin with the adhesive solution prior to coating, the problems of Ito et al (U.S. Pat. No. 4,421,737) described above could be avoided. Namely, in Ito et al, a tackified rubber-based adhesive is first coated onto a backing, and the nitroglycerin must be added in a separate step, which requires that the coatings come into intimate contact while aging the material at an elevated temperature. The Ito et al manufacturing process would be highly labor intensive and would be subject to variation from lot to lot, which are problems avoided by the manufacturing method of the present invention.

Also, the manufacturing method of the present invention avoids the problems of Sablotsky (PCT Application WO 86/00814) as described above. Specifically, Sablotsky employs a thermally activated catalyst to crosslink the acrylic adhesive, and the heat required to activate the catalyst results in a loss of nitroglycerin during processing due to volatilization, causing the nitroglycerin content to vary in the finished product and leading to a very hazardous situation. By employing a self-crosslinking acrylic-based adhesive solution, the present inventors discovered that the problems caused by using a thermally activated catalyst to crosslink the acrylic adhesive can be avoided, since the curing can occur at a temperature well below the boiling point of nitroglycerin.

In the manufacturing method of the present invention, the adhesive solution is mixed with an amount of the active drug sufficient to provide the desired final active drug content. For example, in a preferred embodiment of the present invention, the amount of nitroglycerin mixed with the adhesive solution should be sufficient to provide a final nitroglycerin content after drying of 50–65% w/w. The amount of nitroglycerin to be mixed with the adhesive solution can vary, depending on, for example, the solids content of the adhesive solution. The nitroglycerin can be mixed with the adhesive solution for a period of time ranging from, for example, 10 minutes to 90 minutes.

With respect to the coating and drying steps in the manufacturing method of the present invention, the active drug-adhesive mixture can be coated in an amount sufficient to yield, for example, a 1 mil thick coating after drying. The drying step is used to drive off the solvent from the coated layer, with the adhesive being cured at the same time. The drying step desirably should not be carried out at a temperature above the boiling point of the active drug or inactive excipient (e.g., permeation enhancer), so that significant vaporization of the active drug or inactive excipient will not occur and the active drug content or inactive excipient content in the final product can be more easily controlled. Also, while the adhesive may be curable at room temperature, such a temperature may not be satisfactory in terms of the time required or the final product obtained.

Thus, the drying step can be performed at a temperature ranging from, for example, 50° C. to 87° C., preferably 70° C. to 80° C., for a period of time ranging from, for example, 3 minutes to 7 minutes, preferably 4 minutes to 5 minutes. The coating and drying steps can be repeated as necessary to provide a particular active drug-containing adhesive layer thickness desired for the final product.

In the manufacturing method of the present invention, a self-crosslinking acrylic-based adhesive solution can be mixed with a chemically compatible solvent, and the resulting solution can be mixed with the active drug. The use of a solvent is particularly advantageous for nitroglycerin embodiments. By adding the solvent, the nitroglycerin can be present in the nitroglycerin-adhesive mixture in a lower concentration (e.g., at most 20% by weight on a wet basis), thereby making handling and processing operations safer, while still allowing nitroglycerin to be present at a high concentration (e.g., 50% by weight on a dry basis) in the final product after the solvent is driven off during the drying step. Suitable solvents which can be added to the self-crosslinking acrylic-based adhesive solution include organic solvents such as alkyl acetates (e.g., ethyl acetate), acetone, ethanol, isopropanol, hexane, and toluene. For example, glycol monomethyl ethers, $C_1$ to $C_6$ acetate esters, furans (e.g., dioxane, tetrahydrofuran), and $C_1$ to $C_5$ aliphatic linear and branched chain alcohols are solvents which can be used.

The present invention will now be illustrated in further detail by way of the following examples. It should be noted, though, that these examples are not to be construed as limiting the present invention in any way. Unless otherwise indicated, all parts, percents, ratios, and the like are by weight.

EXAMPLE I

A nitroglycerin-adhesive mixture was prepared by mixing 43 weight % ethyl acetate with 57 weight % acrylic acid ester multipolymer solution sold under the designation GMS 2465 by Monsanto Company and subsequently adding nitroglycerin into the above mixture at 20 weight percent of the total formulation weight (the ethyl acetate was added to make the handling and processing safer). The resulting mixture was coated onto 1 mil thick polyester film and dried at 55° C. for 15 minutes to yield a one mil thick coating. Three one mil thick coatings were combined to yield a three mil thick product, discounting the polyester film. Further details of this example and other examples are tabulated near the end of the specification.

The flux values of the invention embodiments were compared to the Key Pharmaceuticals Nitro-Dur® nitroglycerin transdermal system (0.2 mg/hr, 4.0 mg/10 cm²), which has a flux value of 31.1 µg/cm²/hr. The Nitro-Dur® system was suitable to use for the comparison system, because it has a monolithic design (like the invention system) and because it carries the same drug load (40 mg nitroglycerin content) used in the determination of the flux values in the invention embodiments.

Flux was measured from permeation studies using human cadaver skin in an in vitro experiment in which the amount of active compound was measured as it diffused from the transdermal system through the cadaver skin. The transdermal system (either the entire patch or a designated size cut out) was placed on human cadaver skin mounted on a Franz cell. Samples of drug receptor solution were removed periodically and analyzed for drug content. The Franz cell was temperature controlled throughout the entire experiment. Flux values were calculated from the steady-state portion of the concentration/time curve.

The flux values for two runs conducted for this example, as well as the flux values for other examples, are tabulated at the end of the specification (different runs were conducted in one example to demonstrate the reproducibility of the data for a particular formulation). As can be seen from the results, the present invention provided excellent transdermal delivery performance.

EXAMPLE II

The method of manufacturing of Example I was repeated, except that the following components in the following amounts were used:

37.5 weight % ethyl acetate 62.5 weight % GMS 1753 by Monsanto Company 20 weight % nitroglycerin, based upon total formula weight.

This Example can be modified so that it may also include two one mil thick coatings combined to yield a two mil thick product, discounting the polyester film, and a single one mil thick coating to yield a one mil thick product, discounting the polyester film.

EXAMPLE III

The method of manufacturing of Example I was repeated, except that the following components in the following amounts were used:

39.0 weight % ethyl acetate 61.0 weight % GMS 2257 by Monsanto Company 20 weight % nitroglycerin, based upon total formula weight.

EXAMPLE IV

All formulations from Examples I, II, and III were coated in the following manner. The respective mixture was coated onto a 1 mil thick polyester film and dried at 70° C. for five minutes to yield a 1 mil thick coating. Three one mil thick coatings were combined to yield a three mil thick product, discounting the polyester film.

EXAMPLE V

All formulations from Examples I, II, and III were coated in the following manner. The respective mixture was coated onto a 1 mil thick polyester film and dried at 80° C. for five minutes to yield a 1 mil thick coating. Three one mil thick coatings were combined to yield a three mil thick product, discounting the polyester film.

EXAMPLE VI

All formulations from Examples I, II, and III were coated in the following manner. The respective mixture was coated onto a 1 mil thick polyester film and dried at 87° C. for five minutes to yield a 1 mil thick coating. Three one mil thick coatings were combined to yield a three mil thick product, discounting the ployester film.

EXAMPLE VII

The method of manufacturing of Example I was repeated, except that following components in the following amounts were used:

42 weight % ethyl acetate 58 weight % GMS 1753 by Monsanto Company 19 weight % nitroglycerin, based upon total formula weight.

EXAMPLE VIII

The method of manufacturing of Example I was repeated, except that the following components in the following amounts were used:

45 weight a ethyl acetate 55 weight % GMS 1753 by Monsanto Company 18 weight % nitroglycerin, based upon total formula weight.

EXAMPLE IX

All formulations from Examples I, II, III, VII, and VIII were coated in the following manner. The respective mixture was coated onto a 1 mil thick polyester film and dried at 80° C. for five minutes to yield a 0.8 mil thick coating. Two 0.8 mil thick coatings were combined to yield a 1.6 mil thick product, discounting the polyester film.

EXAMPLE X

All formulations from Examples I, II, III, VII, and VIII were coated in the following manner. The respective mixture was coated onto a 1 mil thick polyester film and dried at 80° C. for five minutes to yield a one mil thick coating. Two one mil thick coatings were combined to yield a two mil thick product, discounting the polyester film.

Alternatively, the coating could be dried at 80° C. for 1.5 minutes or at 80° C. for three minutes to yield a one mil thick coating and subsequently combined to yield a two mil thick product, discounting the polyester film.

EXAMPLE XI

All formulations from Examples I, II, III, VII, and VIII were coated in the following manner. The respective mixture was coated onto a 1 mil thick polyester film and dried at 80° C. for five minutes to yield a 1.2 mil thick coating. Two 1.2 mil thick coatings were combined to yield a 2.4 mil thick product, discounting the polyester film.

EXAMPLE XII

All formulations from Examples I, II, III, VII, and VIII were coated in the following manner. The respective mixture was coated onto a 1 mil thick polyester film and dried at 80° C. for 1.5 minutes to yield a singular two mil thick product, discounting the polyester film.

Alternatively, the coating could be dried at 80° C. for five minutes or at 80° C. for three minutes to yield a singular two mil thick product, discounting the polyester film.

EXAMPLE XIII

All formulations from Examples I, II, III, VII, and VIII were coated in the following manner. The respective mixture was coated onto a 1 mil thick polyester film and dried at 82°–83° C. for three minutes to yield a singular two mil thick coating as the final product.

Additionally, the mixture could be dried at 83° C. for 1.5 minutes or at 83° C. for five minutes to yield a singular two mil thick coating as the final product. Alternatively, the coating could be dried at 82°–83° C. for 1.5 minutes or at 82°–83° C. for five minutes to yield a one mil thick coating and subsequently combined to yield a two mil thick product, discounting the polyester film.

EXAMPLE XIV

All formulations from Examples I, II, III, VII, and VIII were coated in the following manner. The respective mixture was coated onto a 1 mil thick polyester film and dried at 86° C. for three minutes to yield a singular two mil thick coating as the final product. Additionally, the mixture could be dried at 86° C. for 1.5 minutes or at 86° C. for five minutes to yield a singular two mil thick coating as the final product.

Alternatively, the coating could be dried at 86° C. for 1.5 minutes or at 86° C. for five minutes to yield a one mil thick coating and subsequently combined to yield a two mil thick product, discounting the polyester film.

EXAMPLE XV

All formulations from Examples I, II, III, VII, and VIII were coated in the following manner. The respective mixture was coated onto a 1 mil thick polyester film and dried at 54° C. for three minutes and then at 80° C. for three minutes to yield a singular two mil thick coating as the final product, discounting the polyester film.

EXAMPLE XVI

All formulations from Examples I, II, III, VII, and VIII were coated in the following manner. The respective mixture was coated onto a 1 mil thick polyester film and dried at 54° C. for 1.7 minutes, followed by drying at 68° C. for 1.7 minutes and finally drying at 81° C. for 1.7 minutes. The final dry coating thickness was two mils for the product, discounting the polyester film.

EXAMPLE XVII

A method of manufacture which is the same as described in Example XVI may be used to yield a final dry coating thickness of 2.5 mils for the product, discounting the polyester film.

EXAMPLE XVIII

A method of manufacture which is the same as described in Example XVI may be used to yield a final dry coating thickness of three mils for the product, discounting the polyester film.

EXAMPLE XIX

All formulations from Examples I, II, III, VII, and VIII were coated in the following manner. The respective mixture was coated onto a 1 mil thick polyester film and dried at 80° C. for five minutes to yield a singular three mil thick product, discounting the polyester film.

EXAMPLE XX

All formulations from Examples I, II, III, VII, and VIII were coated in the following manner. The respective mixture was coated onto a 1 mil thick polyester film and dried at 80° C. for five minutes to yield a singular 2.8 mil thick product, discounting the polyester film.

EXAMPLE XXI

All formulations from Examples I, II, III, VII, and VIII were coated in the following manner. The respective mixture was coated onto a 1 mil thick polyester film and dried at 80° C. for five minutes to yield a singular 3.2 mil thick product, discounting the polyester film.

EXAMPLE XXII

The method of manufacturing of Examples XVIII and XX was repeated, except that the following components in the following amounts were used:

49.7 weight % ethyl acetate
11.8 weight % GMS 1753 by Monsanto Company
38.5 weight % GMS 1430 by Monsanto Company
20 weight % nitroglycerin, based upon total formula weight.

EXAMPLE XXIII

The method of manufacturing of Examples XVIII and XX was repeated, except that the following components in the following amounts were used:

47.4 weight % ethyl acetate
23.7 weight % GMS 1753 by Monsanto Company
28.9 weight % GMS 1430 by Monsanto Company
20 weight % nitroglycerin, based upon total formula weight.

EXAMPLE XXIV

The method of manufacturing of Examples XVIII and XX was repeated, except that the following components in the following amounts were used:

45.2 weight % ethyl acetate
35.5 weight % GMS 1753 by Monsanto Company
19.3 weight % GMS 1430 by Monsanto Company
20 weight % nitroglycerin, based upon total formula weight.

EXAMPLE XXV

The method of manufacturing of Example XX was repeated, except that the following components in the following amounts were used:

43.0 weight % ethyl acetate
47.4 weight % GMS 1753 by Monsanto Company
9.6 weight % GMS 1430 by Monsanto Company
20 weight % nitroglycerin, based upon total formula weight.

EXAMPLE XXVI

The method of manufacturing of Example XVIII was repeated, except that the following components in the following amounts were used:

46.3 weight % ethyl acetate
29.6 weight % GMS 1753 by Monsanto Company
24.1 weight % GMS 1430 by Monsanto Company
20 weight % nitroglycerin, based upon total formula weight.

EXAMPLE XXVII

The method of manufacturing of Example XVIII was repeated, except that the following components in the following amounts were used:

48.5 weight % ethyl acetate
17.8 weight % GMS 1753 by Monsanto Company
33.7 weight % GMS 1430 by Monsanto Company
20 weight % nitroglycerin, based upon total formula weight.

EXAMPLE XXVIII

The method of manufacturing of Example XVIII was repeated, except that the following components in the following amounts were used:

46.9 weight % ethyl acetate 26.6 weight % GMS 1753 by Monsanto Company 26.5 weight % GMS 1430 by Monsanto Company 20 weight % nitroglycerin, based upon total formula weight.

EXAMPLE XXIX

An estradiol-adhesive solution mixture was prepared by mixing 0.2 weight % estradiol with 0.7 weight % propylene glycol, 2.0 weight % hexylene glycol, and 1.8 weight % isopropyl palmitate and subsequently mixing 95.3 weight % acrylic acid ester multipolymer solution, sold under the designation GMS 1753 by Monsanto Company, into the above-described mixture. The resulting mixture was coated onto 1 mil polyurethane film and dried at 60° C. for 5 minutes to yield a 1.5 mil thick coating. Three 1.5 mil thick coatings were combined to yield a 4.5 mil thick product, discounting the polyurethane film.

EXAMPLE XXX

The method of manufacturing of Example XXIX was repeated, except that the following components in the following amounts were used:

0.35 weight % estradiol 1.4 weight % propylene glycol 3.85 weight % hexylene glycol 3.5 weight % isopropyl palmitate 90.9 weight % GMS 1753 based upon total formula weight.

EXAMPLE XXXI

The method of manufacturing of Example XXIX was repeated, except that the following components in the following amounts were used:

0.5 weight % estradiol 2.0 weight % propylene glycol 5.5 weight % hexylene glycol 5.0 weight % isopropyl palmitate 87.0 weight % GMS 1753 based upon total formula weight.

EXAMPLE XXXII

A mixture was prepared from the following components used in the following amounts:

0.8 weight % estradiol 4.9 weight % propylene glycol 7.3 weight % hexylene glycol 87.0 weight % GMS 1753 based upon total formula weight. The mixture was coated onto 3 mil polyester film and dried at 60° C. for 5 minutes to yield a 1.5 mil thick coating. Three 1.5 mil thick coatings were combined to yield one 4.5 mil thick product, discounting the polyester film.

EXAMPLE XXXIII

The method of manufacturing of Example XXXII was repeated, except that the following components in the following amounts were used:

1.0 weight % estradiol 5.8 weight % propylene glycol 8.7 weight % hexylene glycol 84.5 weight % GMS 1753 based upon total formula weight.

EXAMPLE XXXIV

The method of manufacturing of Example XXXII was repeated, except that the following components in the following amounts were used:

0.9 weight % estradiol 5.4 weight % propylene glycol 8.0 weight % hexylene glycol 85.7 weight % GMS 1753 based upon total formula weight.

EXAMPLE XXXV

A mixture was prepared from the following components used in the following amounts:

0.7 weight % estradiol 4.1 weight % propylene glycol 6.1 weight % hexylene glycol 59.1 weight % GMS 1753

30.0 weight % ethyl acetate based upon total formula weight. The mixture was coated onto 0.7 mil polypropylene film and dried at 54° C. for 1.7 minutes, followed by drying at 66° C. for 1.7 minutes followed by drying at 107° C. for 1.7 minutes to yield a 2.5 mil thick coating. Two 2.5 mil thick coatings were combined to yield one 5.0 mil thick product, discounting the polypropylene film.

EXAMPLE XXXVI

The formulation from Example XXXV was dried at 54° C. for 1.7 minutes, followed by drying at 68° C. for 1.7 minutes, followed by drying at 81° C. for 1.7 minutes to yield a 2.5 mil thick coating. Two 2.5 mil thick coatings were combined to yield one 5.0 mil thick product, discounting the polypropylene film.

EXAMPLE XXXVII

A mixture was prepared from the following components used in the following amounts:

1.0 weight % estradiol 5.8 weight % propylene glycol 8.7 weight % hexylene glycol 84.5 weight % GMS 1753 based upon total formula weight. The mixture was coated onto polypropylene film and dried at 60° C. for 5 minutes to yield a 2.5 mil thick coating. Two 2.5 mil thick coatings were combined to yield one 5.0 mil thick product, discounting the polypropylene film. Separately, 100 weight % acrylic acid ester multipolymer solution sold under the designation GMS 1753 by Monsanto Company was coated onto a 1.5 mil siliconized polyester release liner and dried to yield a 2.0 mil thick coating, discounting the polyester release liner. A 1.25 mil 18% ethylene methyl acrylate (EMA) film was then cold-nipped to this adhesive coating. This laminate (EMA film side) was then cold-nipped to the above-described product.

EXAMPLE XXXVIII

The formulation from Example XXXVII was coated in the following manner: The mixture was coated onto a polypropylene film and dried at 60° C. for 5 minutes to yield a 2.0 mil thick coating. Two 2.0 mil thick coatings were combined to yield one 4.0 mil thick product, discounting the polypropylene film. Separately, 100 weight % acrylic acid ester multipolymer solution sold under the designation GMS 1753 by Monsanto Company was coated onto a 1.5 mil siliconized polyester release liner and dried to yield a 2.0 mil thick coating, discounting the polyester release liner. A 1.25 mil EMA film was then cold-nipped to this adhesive coating. This laminate (EMA film side) was then cold-nipped to the above-described product.

EXAMPLE XXXIX

A mixture was prepared from the following components used in the following amounts:

0.3 weight % estradiol 5.9 weight % neodecanoic acid 23.8 weight % propylene glycol 70.0 weight % GMS 1753 based upon total formula weight. The mixture was coated onto a polypropylene film and dried at 60° C. for 5 minutes to yield a 2.5 mil thick coating. Two 2.5 mil thick coatings were combined to yield one 5.0 mil thick product, discounting the polypropylene film.

EXAMPLE XL

The method of manufacturing of Example XXXIX was repeated, except that the following components in the following amounts were used:

0.15 weight % estradiol 3.0 weight % neodecanoic acid 11.85 weight % propylene glycol 85.0 weight % GMS 1753 based upon total formula weight.

EXAMPLE XLI

The method of manufacturing of Example XXXIX was repeated, except that the following components in the following amounts were used:

0.8 weight % estradiol 6.0 weight % propylene glycol 8.7 weight % hexylene glycol 84.5 weight % GMS 1753 based upon total formula weight.

EXAMPLE XLII

The method of manufacturing of Example XXXIX was repeated, except that the following components in the following amounts were used:

0.85 weight % estradiol 6.0 weight % propylene glycol 8.65 weight % hexylene glycol 84.5 weight % GMS 1753 based upon total formula weight.

EXAMPLE XLIII

The method of manufacturing of Example XXXIX was repeated, except that the following components in the following amounts were used:

0.9 weight % estradiol 5.9 weight % propylene glycol 8.7 weight % hexylene glycol 84.5 weight % GMS 1753 based upon total formula weight.

EXAMPLE XLIV

An estradiol-adhesive solution mixture was prepared by mixing 1.0 weight % estradiol with 15.0 weight % saturated polyglycolyzed glycerides solution, sold under the designation Labrasol by Gattefosse, and subsequently mixing 84.0 weight % GMS 1753 into the above-described mixture. The method of manufacture of this formulation was the same as Example XXXIX.

EXAMPLE XLV

An estradiol-adhesive solution mixture was prepared by mixing 2.0 weight % estradiol with 15.0 weight % diethylene glycol monoethyl ether, sold under the designation Transcutol by Gattefosse, and subsequently mixing 83.0 weight % GMS 1753 into the above-described mixture. The method of manufacture of this formulation was the same as Example XXXIX.

TABULATION OF VALUES FOR SELECTED EXAMPLES

| NITROGLYCERIN TRANSDERMAL FORMULATIONS | | | | | |
|---|---|---|---|---|---|
| | I | II | III | VII | VIII |
| 2465 | 704.5 | — | — | — | — |
| 1753 | — | 490.1 | — | 44.4 | 49.4 |
| 2257 | — | — | 632.2 | — | — |
| Ethyl Acetate | 535.0 | 294.1 | 404.6 | 24.2 | 23.0 |
| NTG | 309.9 | 196.1 | 259.2 | 15.9 | 15.6 |
| FLUX | 34.9 | 35.5 | 25.6 | — | — |
| mcg/cm²/hr | 34.6 | 33.4 | 21.8 | — | — |
| Key 31.1 mcg/cm²/hr | | | | | |
| EXAMPLE WET WEIGHT PERCENT | | | | | |
| 2465 | 45.5 | — | — | — | — |
| 1753 | — | 50.0 | — | 52.5 | 56.3 |
| 2257 | — | — | 48.8 | — | — |
| Ethyl Acetate | 34.5 | 30.0 | 31.2 | 28.7 | 26.0 |
| NTG | 20.0 | 20.0 | 20.0 | 18.8 | 17.7 |
| EXAMPLE DRY WEIGHT PERCENT | | | | | |
| 2465 | 50.0 | — | — | — | — |
| 1753 | — | 44.4 | — | 47.2 | 50.3 |
| 2257 | — | — | 50.0 | — | — |
| Ethyl Acetate | — | — | — | — | — |
| NTG | 50.0 | 55.6 | 50.0 | 52.8 | 49.7 |

| | XXV | XXIV | XXVI | XXVIII | XXII | XXVII | XXII |
|---|---|---|---|---|---|---|---|
| EXAMPLE WET WEIGHT PERCENT | | | | | | | |
| 1753 | 39.1 | 29.4 | 24.4 | 21.9 | 19.4 | 14.7 | 9.7 |
| 1430 | 7.7 | 15.3 | 19.3 | 21.2 | 23.2 | 26.9 | 30.9 |
| Ethyl Acetate | 33.4 | 35.5 | 36.5 | 37.1 | 37.6 | 38.6 | 39.6 |
| NTG | 19.8 | 19.8 | 19.8 | 19.8 | 19.8 | 19.8 | 19.8 |
| EXAMPLE DRY WEIGHT PERCENT | | | | | | | |
| 1753 | 35.3 | 26.5 | 22.0 | 19.8 | 17.6 | 13.2 | 8.8 |
| 1430 | 8.8 | 17.6 | 22.1 | 24.3 | 26.5 | 30.9 | 35.3 |
| Ethyl Acetate | — | — | — | — | — | — | — |
| NTG | 55.9 | 55.9 | 55.9 | 55.9 | 55.9 | 55.9 | 55.9 |
| EXAMPLE WEIGHT GRAMS | | | | | | | |
| 1753 | 47.8 | 35.9 | 1434.7 | 4380.9 | 23.8 | 855.0 | 11.9 |
| 1430 | 9.9 | 19.5 | 1177.8 | 4230.7 | 29.4 | 1637.5 | 39.0 |
| Ethyl Acetate | 25.7 | 27.8 | 1264.2 | 7324.5 | 29.7 | 1386.7 | 31.7 |

-continued

NITROGLYCERIN TRANSDERMAL FORMULATIONS

| NTG | 24.4 | 24.6 | 1188.2 | 4033.9 | 24.8 | 1189.0 | 25.0 |
|---|---|---|---|---|---|---|---|
| FLUX (µg/cm²/hr) | | 51.0 | | 54.2 | | 52.0 | |

Thus, the present invention avoids thermal activation of a polymer to produce the desired crosslinked polymer. it avoids excessive thermal exposure which could degrade an active drug (e.g., in the case of nitroglycerin), imbalance the components of the system, and increase the volatilization of an active drug (e.g., in the case of nitroglycerin) or inactive liquid excipient (e.g., permeation enhancer), and it may be used to provide a better controlled delivery of an active drug (e.g., nitroglycerin or estradiol) producing an improved therapeutic response.

While the invention has been described in detail and with reference to specific embodiments thereof, it will be apparent to one skilled in the art that various changes can be made without departing from the spirit and scope thereof.

What is claimed is:

1. A transdermal delivery system comprising a backing layer having coated thereon an active drug-containing adhesive layer consisting of
   (a) an acrylic-based adhesive which is self-crosslinking at a temperature of from about 20° C. to about 65° C., and
   (b) an active drug,
wherein the active drug is contained directly in the adhesive, wherein the active drug-containing adhesive layer is formed by drying a mixture of the active drug and the acrylic-based adhesive coated on the backing layer, and wherein the active drug is nitroglycerin present in an amount of at least 50% by weight, based on the total dry weight of the adhesive layer.

2. A transdermal delivery system as in claim 1, wherein the nitroglycerin is present in an amount of at least 60% by weight, based on the total dry weight of the adhesive layer.

3. A transdermal delivery system as in claim 1, wherein the nitroglycerin is present in an amount of from 50 to 65% by weight, based on the total dry weight of the adhesive layer.

4. A transdermal delivery system as in claim 1, wherein the adhesive is an acrylic multipolymer adhesive.

5. A transdermal delivery system as in claim 1, wherein the adhesive contains esters of $C_4$–$C_{10}$ alkyl alcohols in an amount less than 70% by weight.

6. A transdermal delivery system comprising a backing layer having coated thereon an active drug-containing adhesive layer consisting of
   (a) an acrylic-based adhesive which is self-crosslinking at a temperature of from about 20° C. to about 65° C.,
   (b) an active drug, and
   (c) a permeation enhancer,
wherein the active drug is contained directly in the adhesive, wherein the active drug-containing adhesive Layer is formed by drying a mixture of the active drug and the acrylic-based adhesive coated on the backing layer, wherein the active drug is estradiol present in an amount of at least 1.0% by weight, wherein the permeation enhancer is selected from the group consisting of alkyl methyl sulfoxides, saturated fatty acid alkyl esters, unsaturated fatty acid alkyl esters, cyclic saturated ketones, and $C_1$ to $C_{14}$ aliphatic linear and branched chain alcohols, and wherein the permeation enhancer is present in an amount of from 2 to 5% by weight, based on the total dry weight of the adhesive layer.

7. A transdermal delivery system comprising a backing layer having coated thereon an active drug-containing adhesive layer consisting of
   (a) an acrylic-based adhesive which is self-crosslinking at a temperature of from about 20° C. to about 65° C., and
   (b) an active drug,
wherein the active drug is contained directly in the adhesive, wherein the active drug-containing adhesive layer is formed by drying a mixture of the active drug and the acrylic-based adhesive coated on the backing layer, and wherein the active drug is nicotine present in an amount of at least 0.5% by weight.

8. A transdermal delivery system comprising a backing layer having coated thereon an active drug-containing adhesive layer consisting of
   (a) an acrylic-based adhesive which is self-crosslinking at a temperature of from about 20° C. to about 65° C., and
   (b) an active drug,
wherein the active drug is contained directly in the adhesive, wherein the active drug-containing adhesive layer is formed by drying a mixture of the active drug and the acrylic-based adhesive coated on the backing layer, and wherein the active drug is selected from the group consisting of fentanyl, clonidine, guanfacine, prostaglandins, and benzodiazepines and is present in an amount of at least 0.5% by weight.

9. A transdermal delivery system as in claim 1, wherein the adhesive is self-crosslinking at a temperature of from about 20° C. to about 30° C.

10. A transdermal delivery system as in claim 6, wherein the adhesive is self-crosslinking at a temperature of from about 20° C. to about 30° C.

11. A transdermal delivery system as in claim 7, wherein the adhesive is self-crosslinking at a temperature of from about 20° C. to about 30° C.

12. A transdermal delivery system as in claim 8, wherein the adhesive is self-crosslinking at a temperature of from about 20° C. to about 30° C.

13. A transdermal delivery system as in claim 6, wherein the adhesive is an acrylic multipolymer adhesive.

14. A transdermal delivery system as in claim 7, wherein the adhesive is an acrylic multipolymer adhesive.

15. A transdermal delivery system as in claim 8, wherein the adhesive is an acrylic multipolymer adhesive.

16. A transdermal delivery system as in claim 6, wherein the adhesive contains esters of $C_4$–$C_{10}$ alkyl alcohols in an amount less than 70% by weight.

17. A transdermal delivery system as in claim 7, wherein the adhesive contains esters of $C_4$–$C_{10}$ alkyl alcohols in an amount less than 70% by weight.

18. A transdermal delivery system as in claim 8, wherein the adhesive contains esters of $C_4$–$C_{10}$ alkyl alcohols in an amount less than 70% by weight.

19. A transdermal delivery system as in claim 1, wherein the nitroglycerin is present in an amount of at least 55% by weight, based on the total dry weight of the adhesive layer.

20. A transdermal delivery system as in claim 1, wherein the nitroglycerin is present in an amount of at least 65% by weight, based on the total dry weight of the adhesive layer.

21. A transdermal delivery system as in claim 1, wherein the nitroglycerin is present in an amount of from 55 to 65% by weight, based on the total dry weight of the adhesive layer.

22. A transdermal delivery system as in claim 2, wherein the adhesive is an acrylic multipolymer adhesive.

23. A transdermal delivery system as in claim 2, wherein the adhesive contains esters of $C_4$–$C_{10}$ alkyl alcohols in an amount less than 70% by weight.

24. A transdermal delivery system as in claim 19, wherein the adhesive is an acrylic multipolymer adhesive.

25. A transdermal delivery system as in claim 19, wherein the adhesive contains esters of $C_4$–$C_{10}$ alkyl alcohols in an amount less than 70% by weight.

26. A transdermal delivery system as in claim 20, wherein the adhesive is an acrylic multipolymer adhesive.

27. A transdermal delivery system as in claim 20, wherein the adhesive contains esters of $C_4$–$C_{10}$ alkyl alcohols in an amount less than 70% by weight.

28. A transdermal delivery system as in claim 1, wherein the acrylic-based adhesive contains a metal catalyst.

29. A transdermal delivery system as in claim 6, wherein the acrylic-based adhesive contains a metal catalyst.

30. A transdermal delivery system as in claim 7, wherein the acrylic-based adhesive contains a metal catalyst.

31. A transdermal delivery system as in claim 8, wherein the acrylic-based adhesive contains a metal catalyst.

32. A transdermal delivery system as in claim 1, wherein the adhesive is an acrylic multipolymer adhesive, contains esters of $C_4$–$C_{10}$ alkyl alcohols in an amount less than 70% by weight, and contains a metal catalyst.

33. A transdermal delivery system as in claim 19, wherein the adhesive is an acrylic multipolymer adhesive, contains esters of $C_4$–$C_{10}$ alkyl alcohols in an amount less than 70% by weight, and contains a metal catalyst.

\* \* \* \* \*